US010552650B2

(12) United States Patent
O'Driscoll et al.

(10) Patent No.: US 10,552,650 B2
(45) Date of Patent: Feb. 4, 2020

(54) SYSTEM OF INJECTABLE FULLY-MONOLITHIC WIRELESS BIO-SENSING

(71) Applicant: Verily Life Sciences LLC, South San Francisco, CA (US)

(72) Inventors: Stephen O'Driscoll, San Francisco, CA (US); You Zou, Redwood City, CA (US); Sean Korhummel, San Carlos, CA (US); Peng Cong, Burlingame, CA (US); Kannan Sankaragomathi, San Mateo, CA (US); Alireza Dastgheib, Mountain View, CA (US); Jiang Zhu, Cupertino, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/193,399

(22) Filed: Nov. 16, 2018

(65) Prior Publication Data

US 2019/0130143 A1    May 2, 2019

Related U.S. Application Data

(63) Continuation of application No. 15/697,264, filed on Sep. 6, 2017, now abandoned.
(Continued)

(51) Int. Cl.
*G06K 7/10* (2006.01)
*A61B 5/00* (2006.01)
(Continued)

(52) U.S. Cl.
CPC ........ *G06K 7/10316* (2013.01); *A61B 5/0031* (2013.01); *G06K 19/0709* (2013.01);
(Continued)

(58) Field of Classification Search
CPC ......... G06K 7/10316; G06K 19/07773; G06K 19/0709; H02M 3/07; A61B 5/0031;
(Continued)

(56) References Cited

U.S. PATENT DOCUMENTS 6,198,339 B1    3/2001 Gersbach et al.
7,310,543 B2    12/2007 Smart et al.
(Continued)

FOREIGN PATENT DOCUMENTS

WO    2006010037    1/2006
WO    2011143324    11/2011
WO    2015120324    8/2015

OTHER PUBLICATIONS

U.S. Appl. No. 15/697,264, "Final Office Action", dated Aug. 23, 2018, 9 pages.
(Continued)

*Primary Examiner* — Seung H Lee
(74) *Attorney, Agent, or Firm* — Kilpatrick Townsend & Stockton LLP (57) ABSTRACT

Systems are provided for a wireless system-on-chip (SoC) with integrated antenna, power harvesting, and biosensors. An illustrative SoC can have a dimension of 200 μm×200 μm×100 μm to allow painless injection. Such small device size is enabled by: a 13 μm×20 μm 1 nA current reference, optical clock recovery, low voltage inverting dc-dc to enable use of higher quantum efficiency diodes, on-chip resonant antenna, and an array-scanning reader.

14 Claims, 12 Drawing Sheets

Related U.S. Application Data (60) Provisional application No. 62/393,078, filed on Sep. 11, 2016.

(51) Int. Cl.
  *G06K 19/07* (2006.01)
  *G06K 19/077* (2006.01)
  *H02M 3/07* (2006.01)
  *A61B 5/145* (2006.01)
  *A61B 5/1473* (2006.01)

(52) U.S. Cl.
  CPC ........ *G06K 19/07773* (2013.01); *H02M 3/07* (2013.01); *A61B 5/1473* (2013.01); *A61B 5/14532* (2013.01); *A61B 2560/0219* (2013.01); *A61B 2562/028* (2013.01)

(58) Field of Classification Search
  CPC ...... A61B 2562/028; A61B 2560/0219; A61B 5/1473; A61B 5/14532
  See application file for complete search history.

(56) References Cited

U.S. PATENT DOCUMENTS

| | | | |
|---|---|---|---|
| 7,826,408 B1 * | 11/2010 | Vleugels | H04W 88/08 |
| | | | 370/328 |
| 9,011,333 B2 | 4/2015 | Geissler et al. | |
| 9,231,292 B2 | 1/2016 | Koo et al. | |
| 2013/0225944 A1 * | 8/2013 | Greco | A61B 5/04 |
| | | | 600/301 |
| 2017/0164476 A1 | 6/2017 | Shibuya | |

OTHER PUBLICATIONS

U.S. Appl. No. 15/697,264, "Non-Final Office Action", dated Mar. 8, 2018, 10 pages.
Bjorninen et al., "Design of Wireless Links to Implanted Brain-Machine Interface Microelectronic Systems", IEEE Antennas and Wireless Propagation Letters, vol. 11, XP011492819, Jan. 1, 2012, pp. 1663-1666.
International Application No. PCT/US2017/050650, "International Preliminary Report on Patentability", dated Mar. 21, 2019, 7 pages.
International Application No. PCT/US2017/050650, "International Search Report and Written Opinion", dated Nov. 22, 2017, 14 pages.

* cited by examiner

| IC TECHNOLOGY | 60nm CMOS |
|---|---|
| DEVICE SIZE | 200μm x 200μm x 100μm |
| PHOTOVOLTAIC AREA | 135μm x 135μm |
| CIRCUITRY AREA | 125μm x 125μm |
| OPTICAL LINK WAVELENGTH | 900nm |
| CHIP POWER CONSUMPTION | 63nW |
| DEMONSTRATED RANGE | 4mm |
| ANTENNA LOOP AREA | 200μm x 200μm |
| ALIGNMENT WINDOW | 11.2mm DIAMETER CIRCLE |
| CLOCK RECOVERY | |
| AREA | 33μm x 33μm |
| OPERATING RANGE | 0.1MHz TO 2MHz |
| POWER CONSUMPTION | 16nW |
| CURRENT REFERENCE | |
| AREA | 13μm x 20μm |
| OUTPUT CURRENT | 1nA |
| LINEAR TUNING RANGE | < 0.12nA TO > 11nA |
| SUPPLY SENSITIVITY ($I_{out}$/VDD) | 50pA/100mV |
| RIPPLE (SIMULATED) | < 0.15% ACROSS CORNERS |
| POWER CONSUMPTION @ 1nA OUTPUT | 7.4 nW |
| -0.3 TO +1.0V DC-DC CONVERTER | |
| AREA | 88μm x 88μm |
| EFFICIENCY @ 100nA LOAD | 37% |

SYSTEM OF INJECTABLE FULLY-MONOLITHIC WIRELESS BIO-SENSING

CROSS-REFERENCE TO RELATED APPLICATIONS

The present application is a continuation of U.S. patent application Ser. No. 15/697,264, filed Sep. 6, 2017, entitled "SYSTEM OF INJECTABLE FULLY-MONOLITHIC WIRELESS BIO-SENSING:, which claims the benefit of priority of U.S. Provisional Application No. 62/393,078, filed Sep. 11, 2016, entitled "SYSTEM OF INJECTABLE FULLY-MONOLITHIC WIRELESS BIO-SENSING", the full disclosures of each which are incorporated herein in their entireties.

BACKGROUND

Technical Field

The present disclosure generally relates to the field of systems for system-on-chip (SoC). More particularly, and without limitation, the disclosed embodiments relate to systems for injectable wireless smart sensing SoC.

Background Description

A SoC generally refers to an integrated circuit (IC) that integrates all components of a computer or other electronic system into a single chip. The SoC may comprise digital, analog, mixed-signal, and/or radio-frequency functions that are all on a single chip substrate. SoCs have various applications including mobile electronics, medical devices, and bio-sensing.

As an exemplary application, SoCs may be used to monitor health metrics of a person and/or animal. Conventionally, for example, skin hydration and body glucose levels have been monitored using needles in the skin because the skin is a vital organ from which many health metrics may be garnered. But, those needles can cause discomfort and impinge on users' lifestyle.

SUMMARY

There is a need for systems and methods for ongoing monitoring that need to be unobtrusive and not require or reduce maintenance. To this end, monolithic injectable wireless smart sensing SoCs according to the present disclosure may fulfill these requirements. The embodiments of the present disclosure provide systems for SoC bio-sensing. According to an exemplary embodiment of the present disclosure, the system may include: an SoC, and a measurement reader having at least one reader antenna for transmitting a signal to the SoC. In an illustrative embodiment, the measurement reader is not located on the SoC. The SoC in some embodiments may comprise: a receiving antenna for receiving the signal transmitted from the at least one reader antenna; a power supply subsystem powered by the signal received by the receiving antenna; a clock recovery subsystem powered by the signal received by the receiving antenna; and a sensor subsystem. In exemplary embodiments, the power supply subsystem may include a plurality of diodes. Further, the clock recovery subsystem in some embodiments may include a set of diodes. And the sensor subsystem may generate a digital signal for modulating the signal transmitted by the measurement reader antenna.

DETAILED DESCRIPTION

The disclosed embodiments relate to systems for injectable wireless sensing SoCs. Advantageously, the exemplary embodiments allow for a monolithic injectable wireless smart sensing SoC to be designed and injected painlessly into a skin. The SoC is such small (for example, less than or equal to 250 µm on each side) that it is not visible once injected. Embodiments of the present disclosure may be implemented in a SoC system, e.g., a glucose bio-sensing system. Alternatively, embodiments of the present disclosure may be implemented in a method for fabricating a SoC bio-sensing system.

In some embodiments of the present disclosure, the SoC bio-sensing system may be injected in the skin at depths ranging from about 1 mm to about 4 mm depending on applications. Although various SoC bio-sensing systems may be fabricated, some embodiments may be powered by a reader, which is placed above the skin when a measurement is to be made. Other embodiments are powered by ambient light for example, to power UV exposure recording.

In some embodiments, a wireless SoC with integrated antenna, power harvesting, and biosensors, and small dimension (e.g., 200 µm×200 µm×100 µm) is provided to allow painless injection. The small device size may be enabled by, for example, a 13 µm×20 µm 1 nA current reference, an optical clock recovery, a low voltage inverting DC-DC to enable use of higher quantum efficiency diodes, an on-chip resonant antenna, and an array scanning reader.

In some embodiments, in-vivo power and data transfer is demonstrated and linear glucose concentration recordings are provided. Innovative circuit designs are provided to achieve the small size and monolithic integration. Further, a glucose-sensing embodiment of a SoC bio-sensing system may be provided.

Reference will now be made in detail to embodiments and aspects of the present disclosure, examples of which are illustrated in the accompanying drawings. Elements in the drawings are not necessarily drawn to scale.

Figure 1:
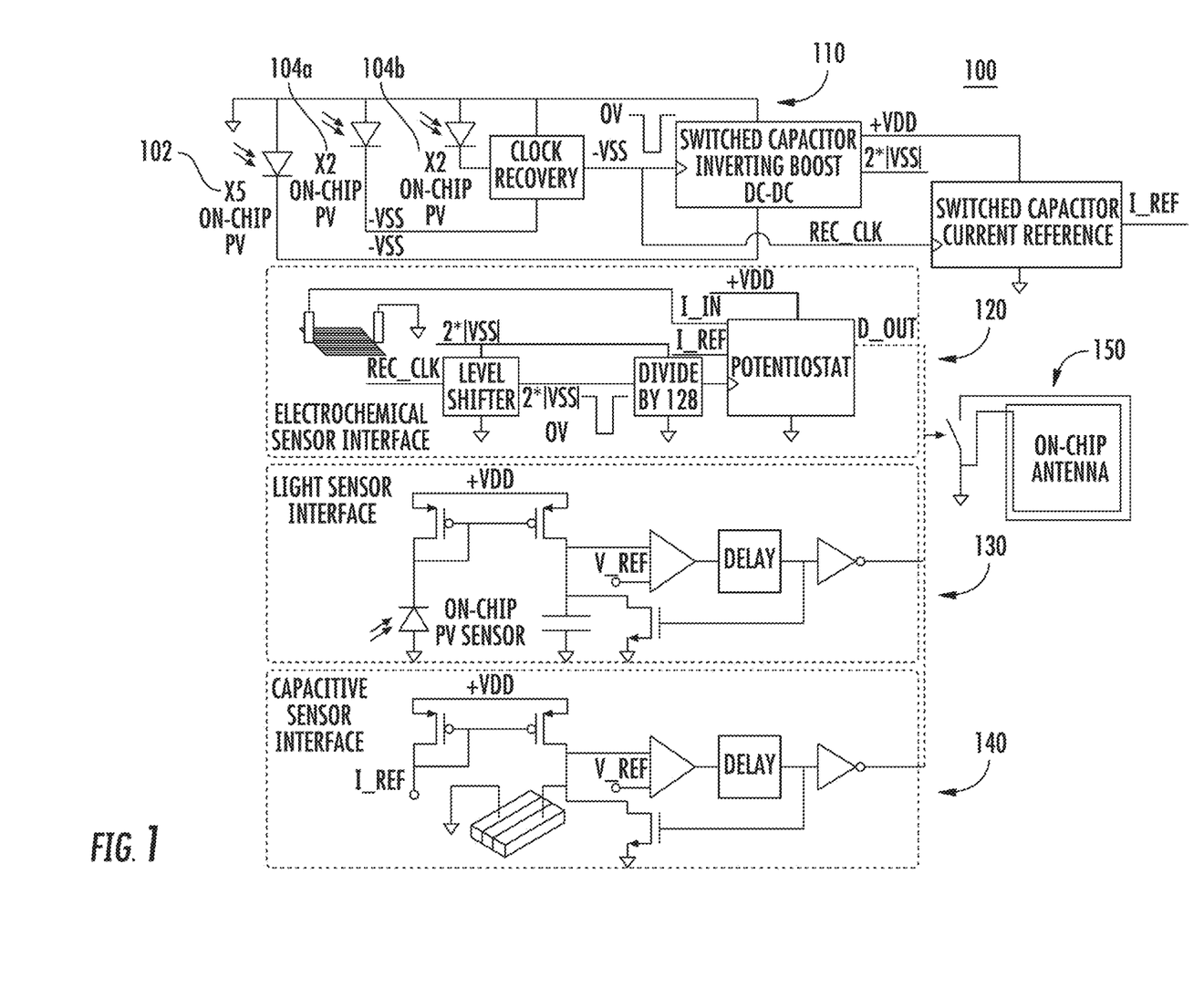
FIG. 1 shows a schematic representation of a monolithic injectable bio-sensing system according to embodiments of the present disclosure.

FIG. 1 is a block diagram of a SoC 100 according to one embodiment of the present application. As shown in FIG. 1, SoC 100 may include a subsystem 110 (a top panel other than dashed boxes illustrated in FIG. 1) showing a scheme to harvest clock and power; an on-chip antenna 150; and various different sensing schemes showed in dashed boxes.

Subsystem 110 may in illustrative embodiment comprise five 44 µm×44 µm on-chip diodes 102 that are used for a main power supply, and four 44 µm×44 µm diodes 104 of which two (104a and 104b) each for a clock recovery supply and an input respectively. The clock and power in subsystem 110 may, for example, be harvested from an amplitude modulated optical signal transmitted by a measurement device reader (referred to as "reader" herein). It is contemplated that other signal diodes may be used.

The reader may transmit a radio frequency (RF) signal. Each sensor interface (i.e., various sensing schemes) generates a digital signal which modulates a load across an impedance of on-chip antenna 150 and thus modulates a reflected RF signal backscattered to the reader.

In an exemplary embodiment, a sensing scheme may be for an electrochemical sensor 120 as shown in FIG. 1. In another embodiment, a sensing scheme may be for a light sensor 130 as shown in FIG. 1. Alternatively, a sensing scheme in FIG. 1 may be for a capacitance sensor 140.

Figure 2A:
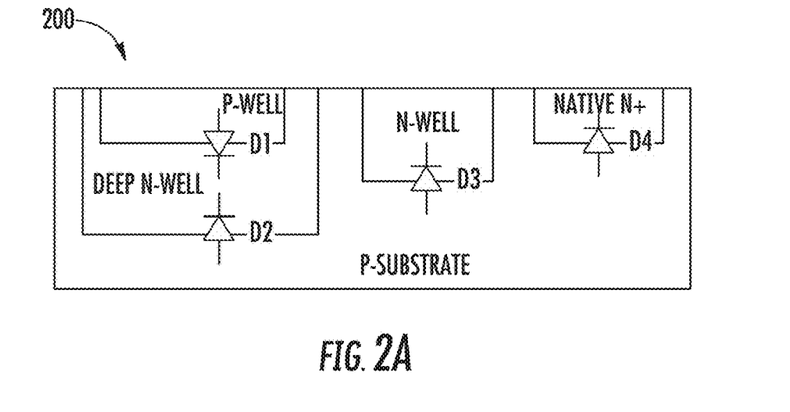
FIGS. 2A-2D show testing of diodes and a schematic representation of a charge pump circuitry used in the system of FIG. 1, according to embodiments of the present disclosure.

As shown in FIG. 1, subsystem 110 may be powered by an optical signal transmitted by the reader. In some embodiments, two major design choices for optical powering are which wavelength of light and which on-chip diodes to use. A diode test structure 200 (referred to as "structure 200" herein) as shown in FIG. 2A, was built to evaluate the two major design choices. Quantum efficiencies of diodes tested in structure 200 are measured and plotted as depicted in a first panel 210 of FIG. 2B. As can be seen, Psub-to-nwell diodes were the most efficient irrespective of wavelength, and thus, Psub-to-nwell diodes (i.e., D3) may be chosen for photovoltaic harvesting. Furthermore, first panel 210 shows higher quantum efficiency at visible wavelengths than in near-IR (infrared).

In addition, optical transmission versus wavelength was evaluated for numerous porcine skin samples. Results for two representative samples are shown in a second panel 220 of FIG. 2B indicating a better transmission in near-IR. This indicates there is a tradeoff between skin-transmission versus diode quantum efficiency.

Figure 2B:
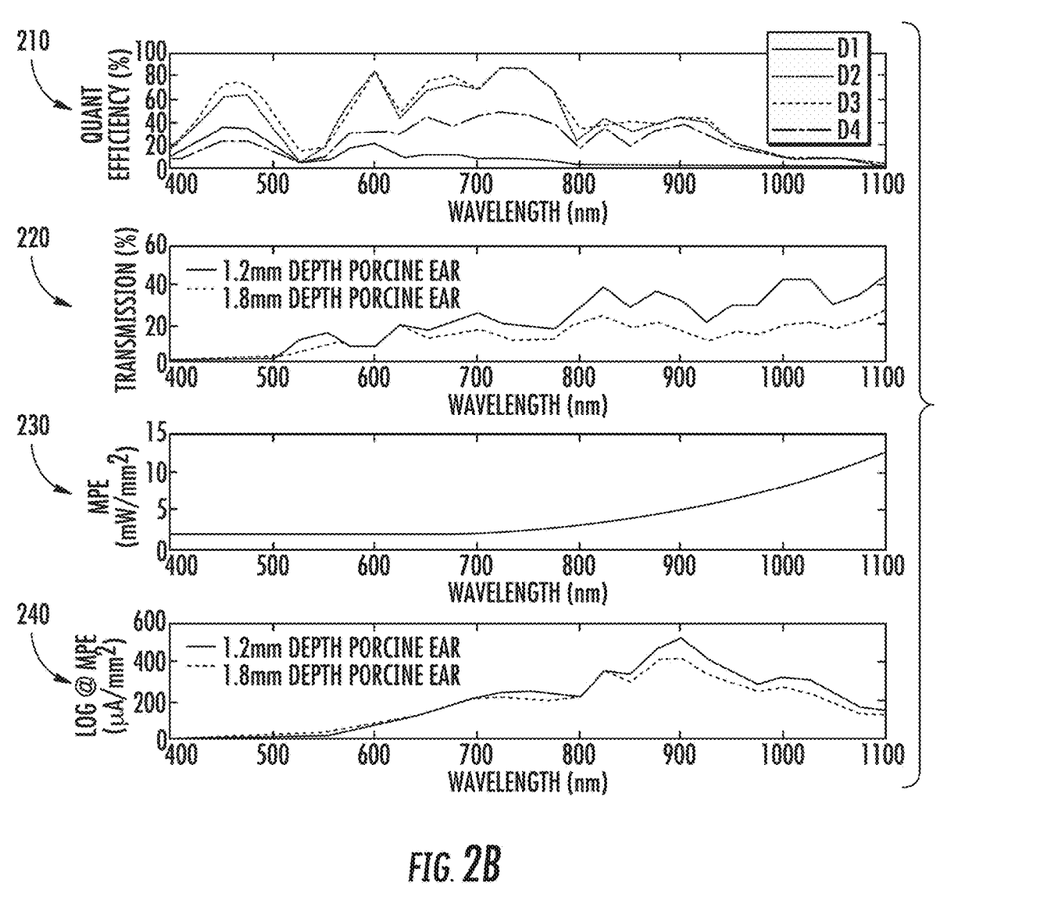

Furthermore, a maximum permissible exposure (MPE) is not uniform across this tested spectrum as shown in a third panel 230 of FIG. 2B. A fourth panel 240 of FIG. 2B shows an available electrical power when operating at the MPE using diodes in this process that is calculated based on the three plots in first panel 210, second panel 220 and third panel 230. Fourth panel 240 also shows that wavelength 900 nm results in the maximum available power on-chip.

While the Psub-to-nwell diodes generate greater available power, they may generate a lower open-circuit voltage than the other diode options. In some embodiments, an input light energy the voltage generated may be −0.3 V. Generating +0.6 V and +1.0 V to supply various on-chip circuits is challenging, not least in the first stage circuits in which the substrate is the most positive potential (for example, 0 V vs −0.3 V).

Figure 2C:
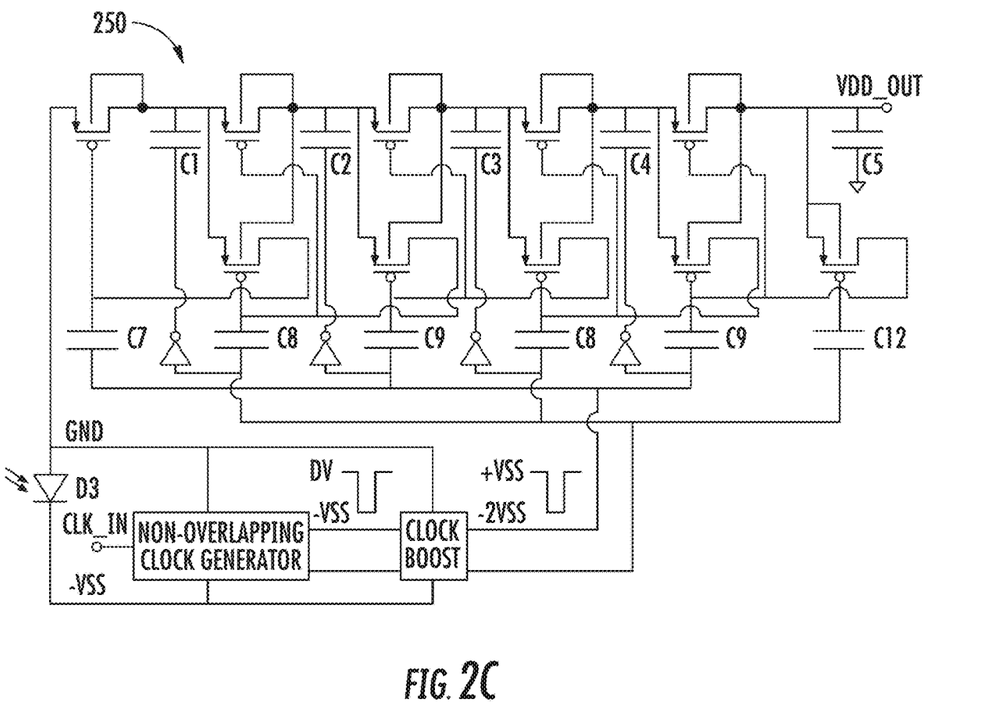
Figure 2D:
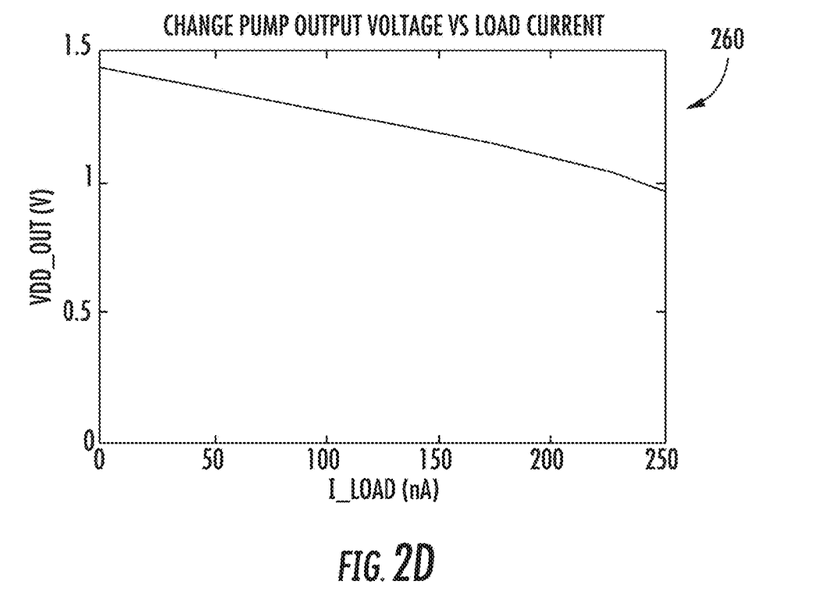

In some embodiments, a DC-DC converter may be used to resolve the above challenge. An exemplary charge pump subsystem 250 is illustrated in FIG. 2C and includes a 3× clock-boosting circuit that generates a clock swing with a peak-to-peak swing of 0.9 V (+0.3 V to −0.6 V) to drive charge pump switches. In this example, all NMOS in the clock booster sit in deep Nwells connected to ground. Switches in the charge pump stages are realized using PMOS transistors, such that deep Nwell NMOS switches are avoided to save area. Switches are bootstrapped using voltages from the successive stages that use the scheme shown in subsystem 250. Nwells of the PMOS are tied to nodes with high capacitance to avoid dropping of the boostrapped gate due to photocurrent of the Nwell-Psub parasitic diode of the PMOS switches. In some embodiments, a top metal optical shield reduces leakage in the parasitic photodiodes. In this example, the input capacitances can be 13 µm×4 µm of MIM (110 pF) per stage input and the per stage output capacitances are 18 µm×22 µm of MIM and MOM per stage output (1.9 pF total per stage). The entire circuit occupies 88 µm×88 µm. A plot 260 of FIG. 2D shows a measured output voltage versus a load current for a charge pump driven by five 44 µm×44 µm on-chip diodes through 3 mm of free space and 1.8 mm of tissue from a 4 mW/mm$^2$ source. As shown in plot 260, the charge pump efficiency at 100 nA load is 37%.

In some embodiments, a current reference may be essential for sensing and current control. A conventional supply independent 1 nA reference may take up a 92 µm×92 µm area, which may be equivalent to one quarter of a total permitted SoC area.

Figure 3A:
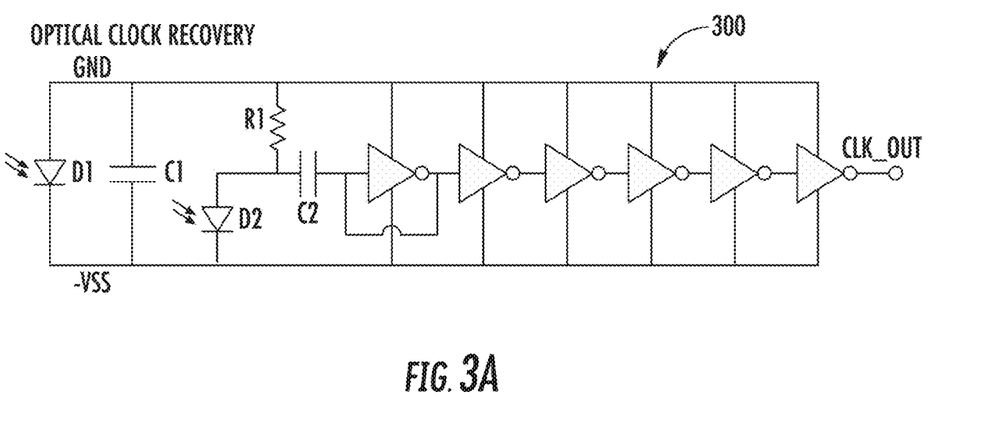
FIGS. 3A-3C show a schematic representation of a clock recovery circuitry used in the system of FIG. 1, according to embodiments of the present disclosure.
Figure 3B:
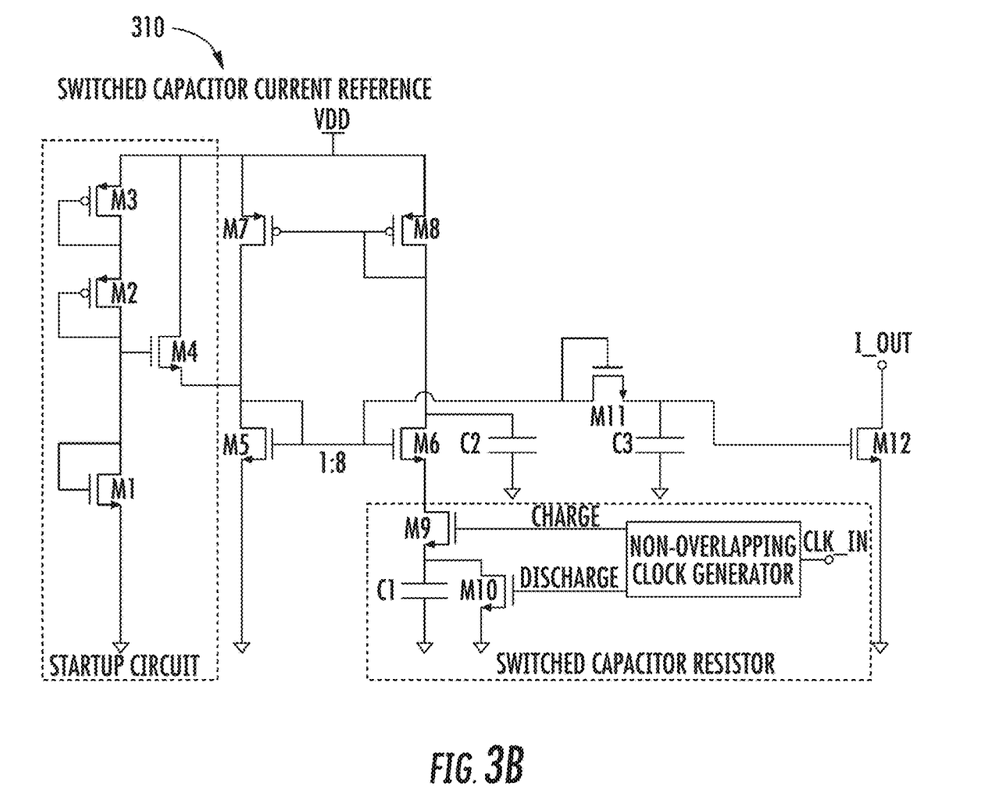

To overcome disadvantages of the conventional approach discussed above, in some embodiments, a switched capacitor reference instead of a conventional physical resistor is used as illustrated in a block diagram 310 of FIG. 3B. In block 310, transistors M5-M8 form a conventional reference. But, a switched capacitor circuit formed by transistors M9 and M10 and a capacitor C1 is applied instead to provide the required resistance. In this example, capacitor C1 is chosen as 20 fF to minimize area whilst ensuring the capacitance is very large with respect to non-linear variations in the switch input capacitance. Startup branch M1-M4 consumes 15 nA at startup and less than 1 pA (e.g., worst case). Pseudoresistor M13 and capacitor C3 form a low pass filter to suppress ripple from the switched capacitor. A simulated output ripple is less than 0.15% across corners as the supply voltage varies from 0.4 V to 1 V. A total area of the switched capacitor circuit may be about 13 µm×20 µm, 32 times less than a conventional resistor alone which would be used in the conventional approach.

Figure 3C:
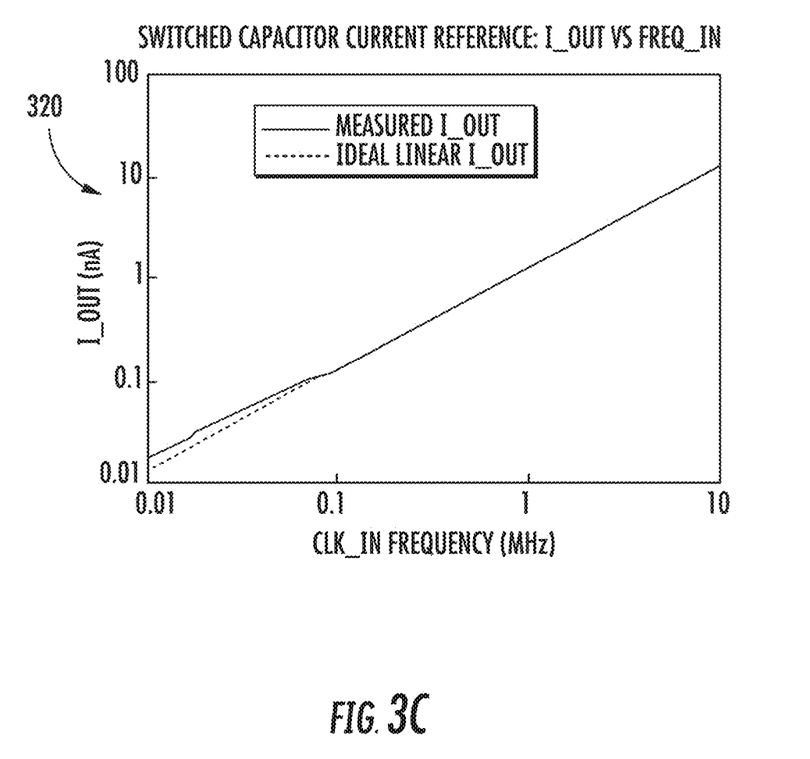

Further shown in FIG. 3C is a plot 320 depicting a plot of measured output current versus input clock frequency. As shown in plot 320, a target current of 1 nA is achieved at an input frequency of 0.8 MHz, and the variation of current with frequency is seen to be linear over more than two decades of frequency. Therefore, the output current can be tuned by varying the input clock frequency which gives flexibility to overcome process variations.

A crystal reference for clock generation would be many times larger than the device. The current reference may require a clock input so clock generation cannot depend on the current reference. Instead, the light transmitted to power the SOC may be amplitude-modulated by the reader. A schematic diagram 300 of an illustrative clock recovery circuit is illustrated in FIG. 3A. In this example, two 44 µm×44 µm N-Well to P-sub diodes D1, are used to generate a supply voltage for the clock recovery circuit. The supply voltage generated is negative, for example, from −0.3 V to −0.4 V. The modulated signal is recovered from an identical diode D2, which is high-pass filtered by a resistor R1 and a capacitor C2 and amplified by the subsequent inverter. The exemplary first inverter is connected in unity-gain feedback. The first stage could be self-biased using a pseudo-resistor and contribute gain, but even with metal light shielding residual light would cause photogeneration in the pseudo-resistor and saturate the inverter. Therefore, in this exemplary design, unity-gain feedback is used for the first stage, but establishes bias for the subsequent stages. Dedicated metal shielding layers on the top of the circuit are employed to reduce offset in the inverter. Metal shielding layers above the circuit may be employed to reduce photo-induced inverter offset. In this example, all NMOS may be deep N-Well with bulk tied to negative voltage source supply (−Vss). The circuit (excluding D1, 2) may occupy 33 μm×33 μm and consumes 45 nA from a −0.35 V supply. In some embodiments, the nominal operating frequency is 1 MHz and the circuit recovers clocks from 0.1 MHz to 2 MHz.

Figure 4A:
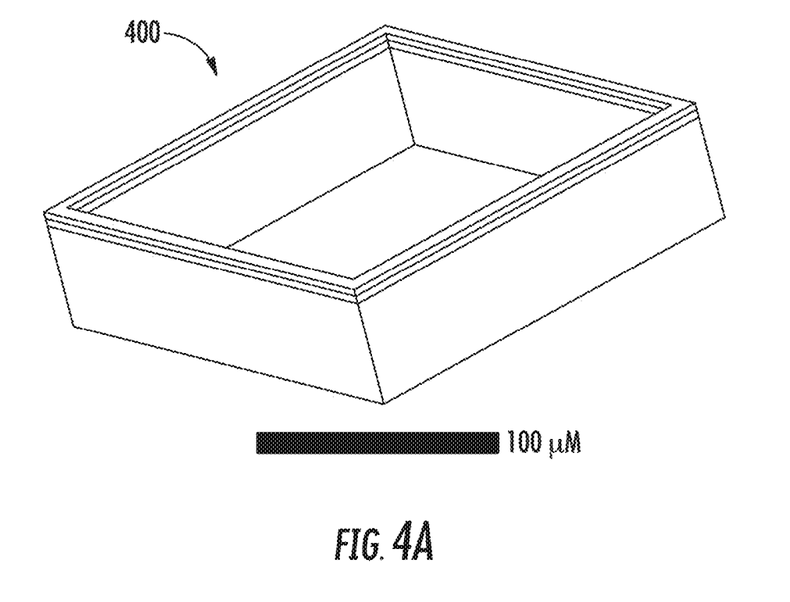
FIGS. 4A-4D show schematic representations of an on-chip antenna and a reader antenna used in the system of FIG. 1, according to embodiments of the present disclosure.
Figure 4B:
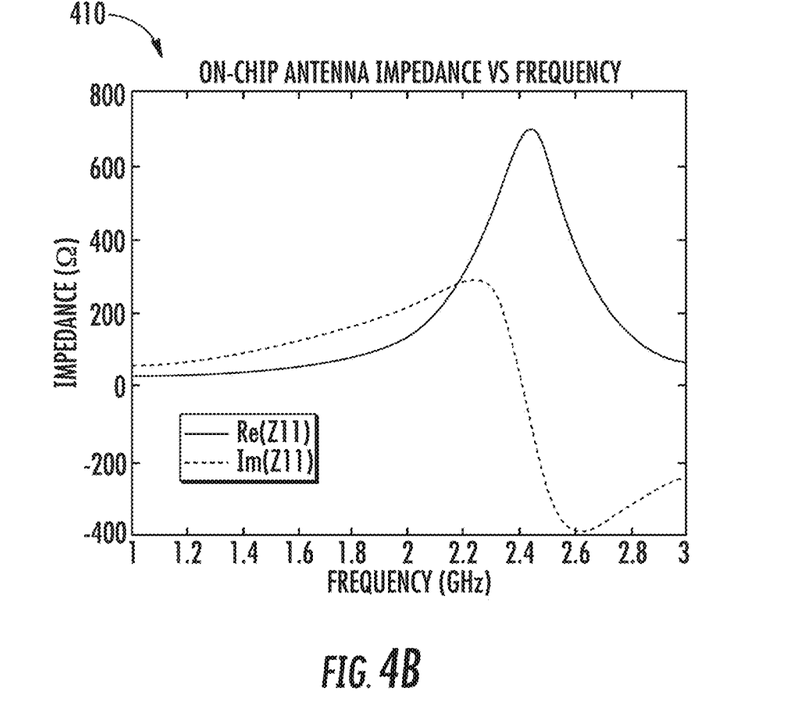

In some embodiments, 2.4 GHz is chosen as an operating frequency for a RF link since an on-chip antenna (also referred to as a receive antenna herein) may be sub-mm sized, which is small compared to the range while being embedded in a lossy tissue. An exemplary on-chip antenna 400 is illustrated in FIG. 4A. For this on-chip antenna, multiple turns over many metal layers give an electrically long structure close to self-resonance thus saving area of matching components and increasing B-field sensitivity. A 25 μm×10 μm MIM capacitor may be used to fine tune. A plot 410 in FIG. 4B illustrates a plot of resulting antenna impedance versus frequency obtained from antenna 400.

Figure 4C:
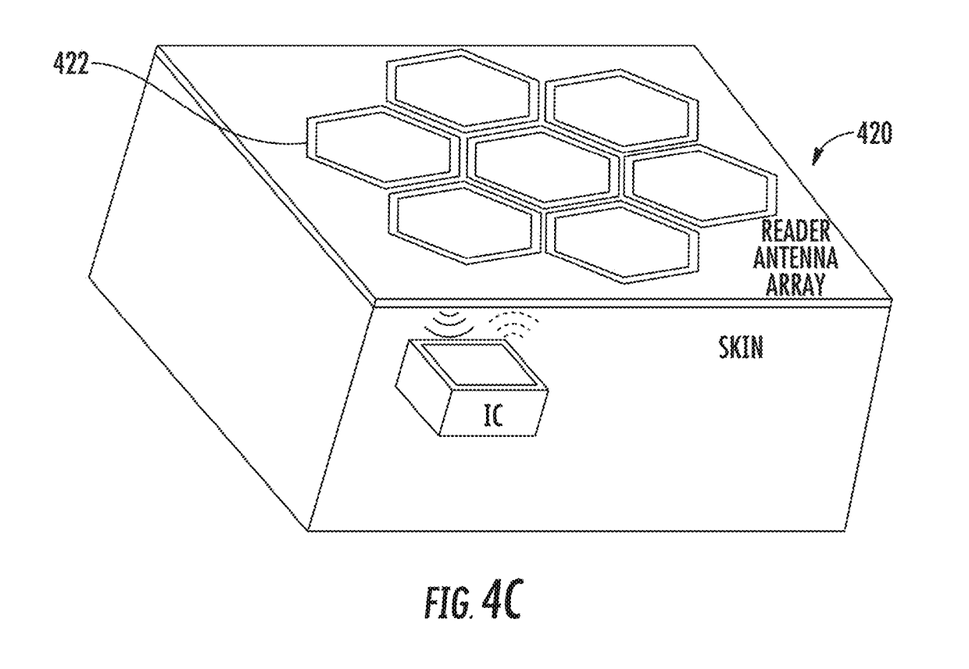
Figure 4D:
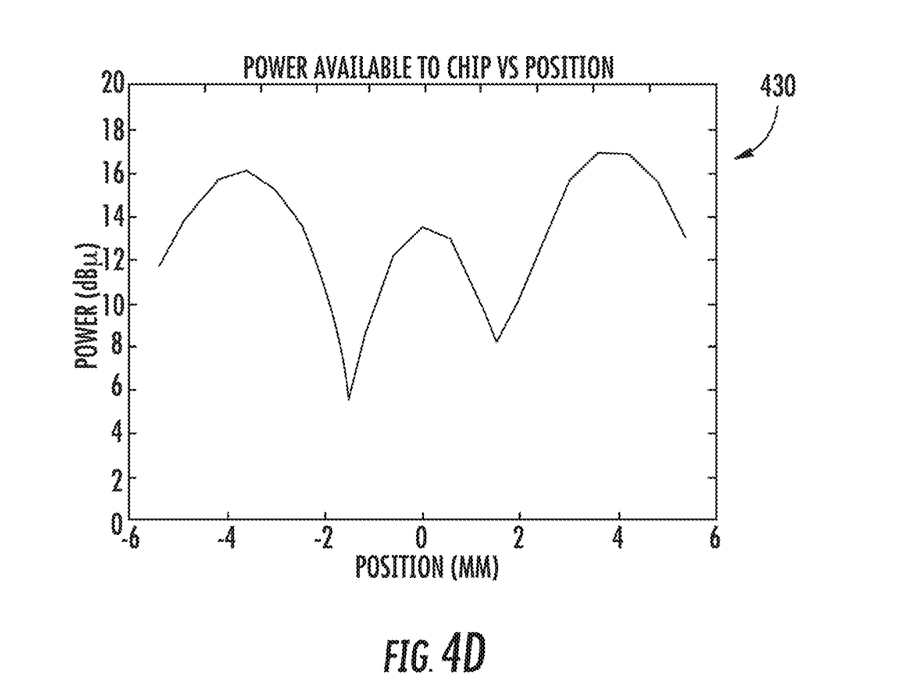

A reader antenna may not be very large compared to a receive antenna in order to maximize link gain making alignment difficult. In some embodiments, a scanning reader antenna array may be used as a reader as illustrated in a diagram 420 in FIG. 4C making alignment easier. As shown in diagram 420 each external antenna element 422 is a hexagon having a diameter of about 3.6 mm and the reader scans through each element 422 to find a best link. Light is transmitted through holes in the middle of each antenna element 422. Power received for RF-powered SoCs at 1.4 mm depth in chicken skin is illustrated a plot 430 in FIG. 4D. To produce plot 430, RX power is measured on an illustrative chip variant. Plot 430 shows power versus postion moving along a diameter of the array at 1.4 mm depth in chicken skin. A scanning link may be used for communication in the optically-powered versions and to power RF-powered versions.

Figure 5A:
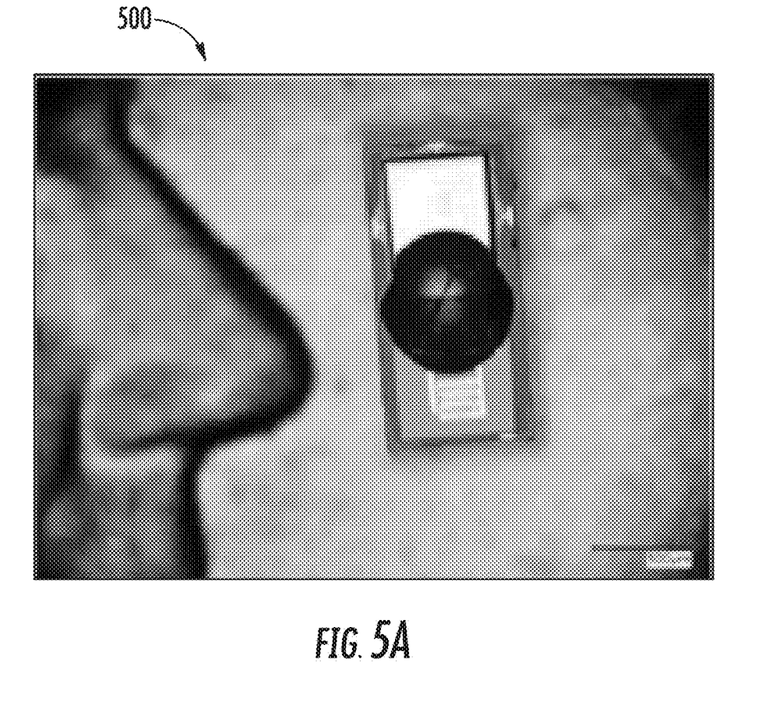
FIGS. 5A-5C show a schematic illustration for an exemplary SoC bio-sensing system with an electrochemical sensor for glucose monitoring, according to embodiments of the present disclosure.
Figure 5B:
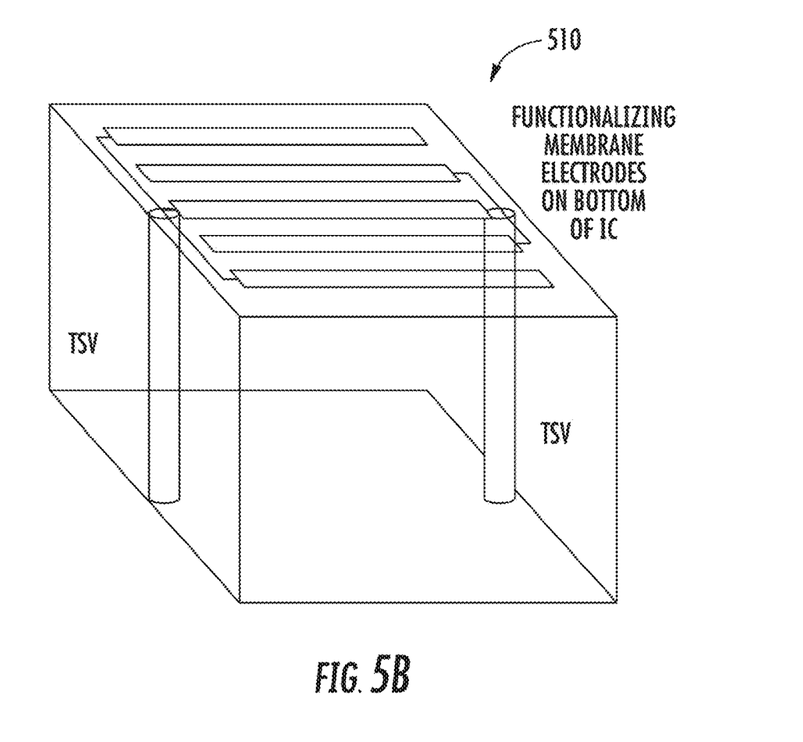

An illustrative electrochemical sensing system is illustrated in a schematic diagram 500 of FIG. 5A according to some embodiments of the present application. As shown in diagram 500, the electrochemical sensing system may be implemented on a larger die to accommodate bond pads. The die may be affixed to a 1.5 mm×0.7 mm glass slide on which a 200 μm×200 μm electrochemical sensor is patterned and functionalized and a potentiostat input is wire bonded to the sensor as shown in FIG. 5A. Such a electrochemical sensor demonstrates the system functionality of a SoC and the feasibility of glucose measurement with such a small sensor. In some embodiments, a SoC may be formed with through-silicon vias and sensors may be fabricated on a backside of the SoC. For example, a schematic diagram 510 of FIG. 5B shows a monolithic glucose sensor with electrode pattern on a bottom side of IC and connected to circuitry through TSVs (through-silicon vias).

Figure 5C:
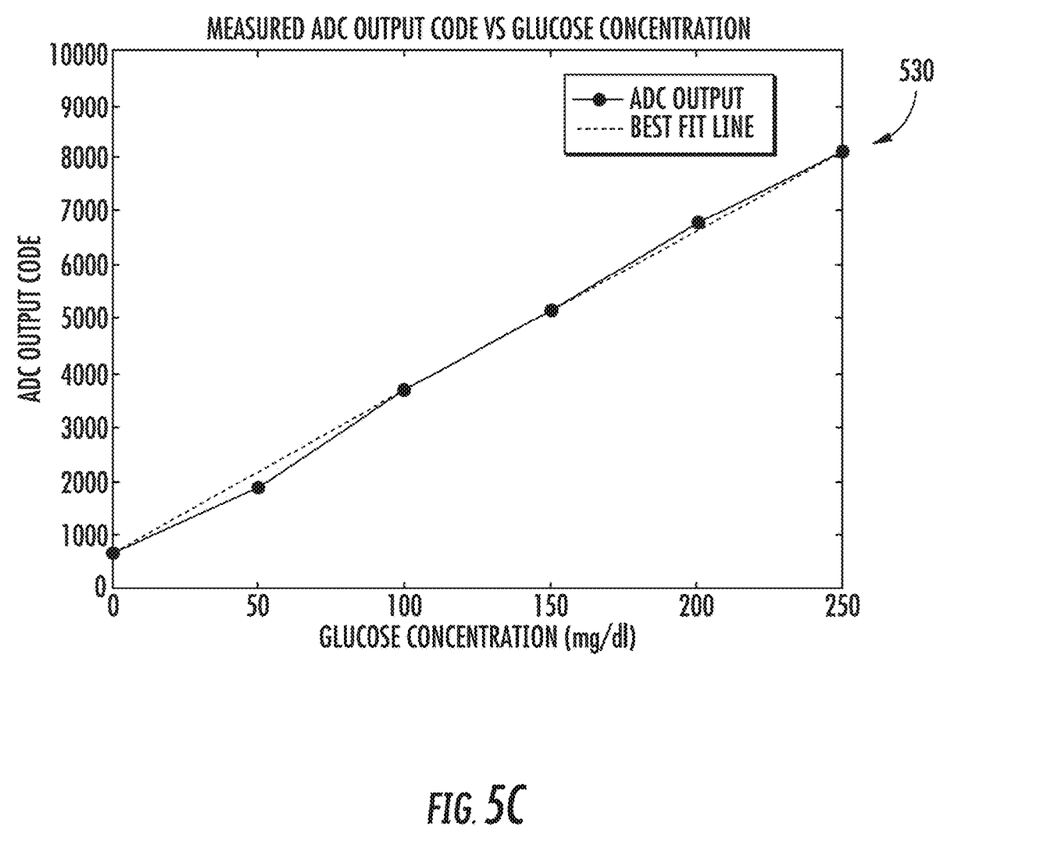

In an illustrative embodiment, a glass slide device is placed in a custom flow cell and controlled concentrations of glucose in saline solution and powered by the reader, which reads the backscatter demodulated ADC output. That recorded ADC output is plotted versus glucose concentration in an illustrative process, as shown in plot 530 of FIG. 5C. A good linearity between ADC output and glucose concentration is observed.

In some embodiments, light sensing systems may be fabricated similarly as the above electrochemical sensing system, which may rely on a source-coupled oscillator to generate the clock and may have higher power consumption.

In some embodiments, capacitance-sensing systems may be fabricated similarly as the above electrochemical sensing system, which may rely on a source-coupled oscillator to generate the clock and may have higher power consumption.

Figure 6A:
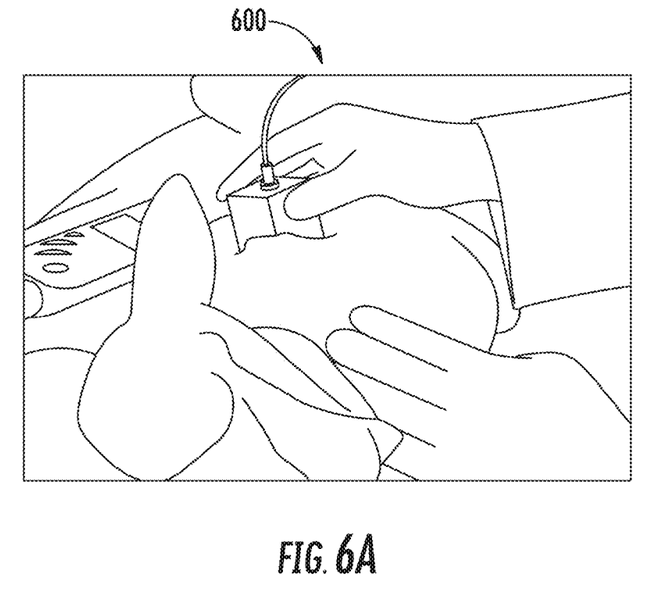
FIGS. 6A-6C show a graphical illustration of the exemplary SoC bio-sensing system and associated performance of the system, according to embodiments of the present disclosure.
Figure 6B:
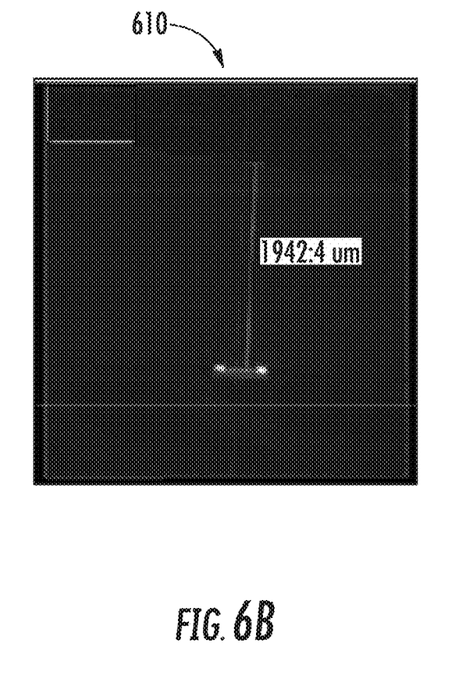

In some embodiments, a SoC device may be coated with a bio-compatible package. A photo 600 of FIG. 6A demonstrates a successful powering and reading at 2 mm depth in-vivo in rabbits using a SoC device coated with the bio-compatible package. Due to an extremely small size, the SoC device can be injected into the skin of a subject with relative ease and with minimal to no pain. A photo 610 of FIG. 6B shows an exvivo SEM image of a SoC device injected into a porcine leg.

Figure 6C:
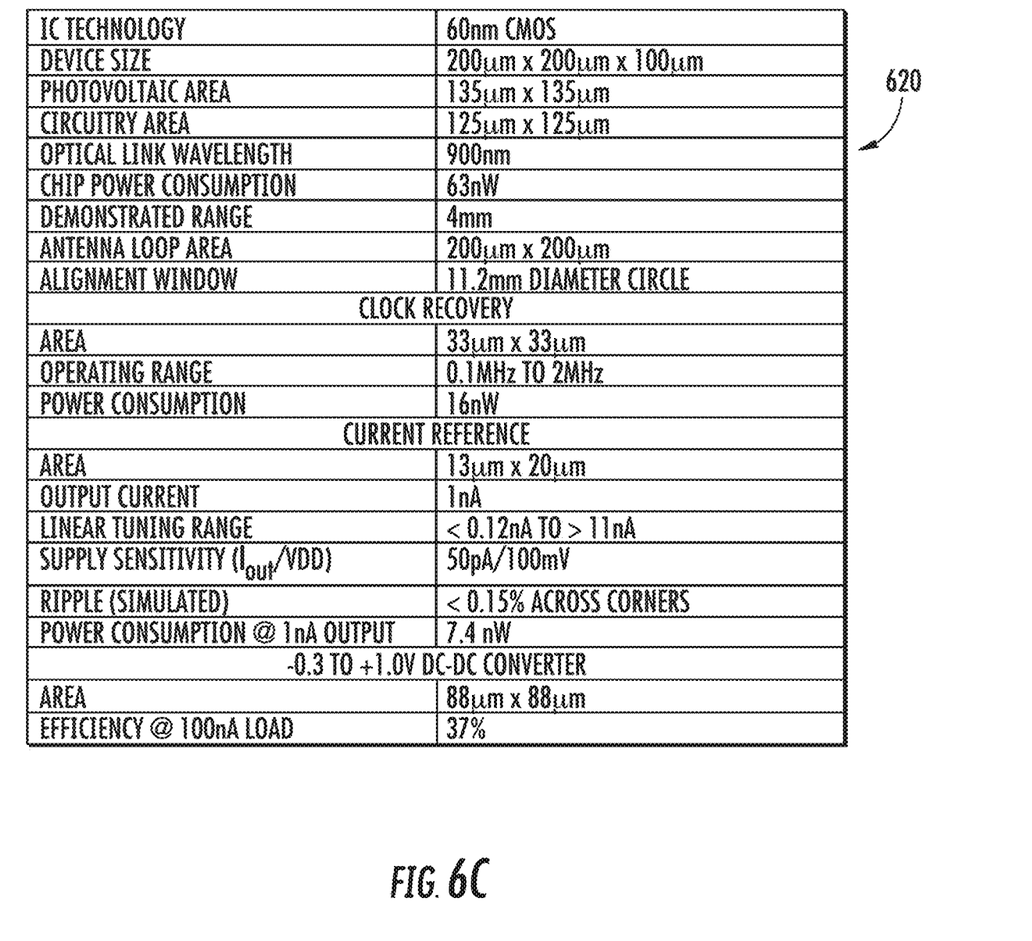

Table 620 of FIG. 6C summarizes further performance information and characteristics of such SoC device for glucose sensing.

Figure 7:
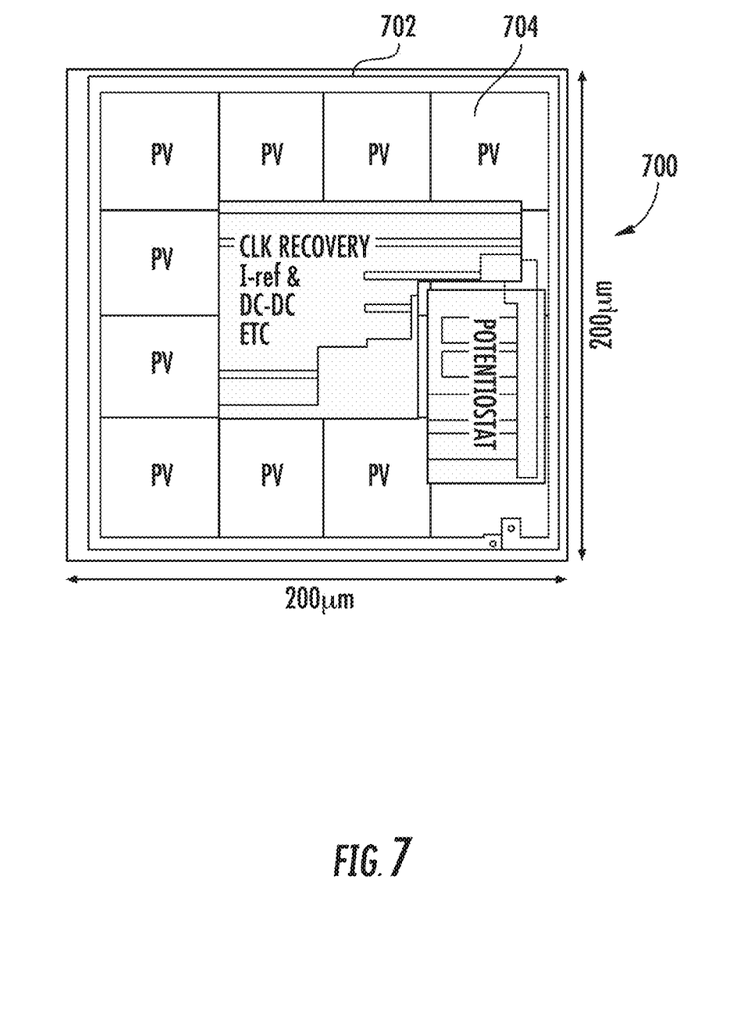
FIG. 7 shows photos of an exemplary die for fabricating a SoC bio-sensing system, according to embodiments of the present disclosure.

FIG. 7 shows photo 700 of a die for fabricating SoC according to some embodiments of the present application. As shown in photo 700, an antenna top layer 702 is visible as a 5 μm wide, 200 μm×200 μm square around the perimeter of the die. Nine squares 704 corresponding to the nine 44 μm×44 μm diodes used for photovoltaic (PV) harvesting of clock and power are visible along the top, left and bottom side of the die. Further, a metal visible above the other circuits is for light shielding. In some embodiments, methods for fabricating the above SoCs may be performed.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and/software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A system-on-chip (SoC) comprising:
 a receiving antenna for receiving a radio-frequency ("RF") signal transmitted radio-frequency ("RF") by a measurement reader;
 a power supply subsystem comprising a first plurality of photodiodes, the first plurality of photodiodes configured to receive an optical signal and to output a first power signal to the power supply subsystem;
 a clock recovery subsystem comprising a second plurality of photodiodes, the first plurality of photodiodes configured to receive the optical signal and to output a second power signal to the clock recovery subsystem; and
 a sensor subsystem, the sensor subsystem configured to modulate a load across an impedance of the receiving antenna.

2. The system of claim 1, wherein the sensor subsystem includes an electrochemical sensor.

3. The system of claim 1, wherein the sensor subsystem includes a light sensor.

4. The system of claim 1, wherein the sensor subsystem includes a capacitance sensor.

5. The system of claim 1, wherein the SoC has a dimension equal to or less than 200 µm×200 µm×100 µm.

6. The system of claim 1, wherein the SoC is injected into a skin at a depth ranging from about 1 mm to about 4 mm.

7. The system of claim 1, wherein the power supply include a charge pump.

8. The system of claim 1, wherein the SoC further comprising a current reference having a switched capacitor reference.

9. The system of claim 1, wherein the SoC further comprises a DC-to-DC voltage converter.

10. The system of claim 1, wherein the power supply subsystem comprises a charge pump, and the first plurality of photodiodes comprises five photodiodes.

11. The system of claim 10, wherein each of the five photodiodes comprises a 44 micron by 44 micron photodiode.

12. The system of claim 10, wherein each of the two photodiodes comprises a 44 micron by 44 micron photodiode.

13. The system of claim 12, wherein the second plurality of photodiodes comprises two photodiodes.

14. The system of claim 1, wherein the optical signal comprises a wavelength between 400 and 1100 nanometers.

* * * * *